(12) United States Patent
Grace

(10) Patent No.: US 8,845,681 B2
(45) Date of Patent: *Sep. 30, 2014

(54) RIGIDLY-LINKED ARTICULATING WRIST WITH DECOUPLED MOTION TRANSMISSION

(71) Applicant: Kenneth Grace, Knoxville, TN (US)

(72) Inventor: Kenneth Grace, Knoxville, TN (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/633,963

(22) Filed: Oct. 3, 2012

(65) Prior Publication Data
US 2013/0030449 A1 Jan. 31, 2013

Related U.S. Application Data

(60) Continuation of application No. 11/948,052, filed on Nov. 30, 2007, now Pat. No. 8,292,916, which is a division of application No. 10/013,170, filed on Jun. 7, 2002, now Pat. No. Re. 43,049, which is a continuation-in-part of application No. 09/262,134, filed on Mar. 3, 1999, now Pat. No. 6,436,107, which is a continuation-in-part of application No. 08/873,190, filed on Jun. 11, 1997, now Pat. No. 6,102,850, which is a continuation-in-part of application No. 08/755,063, filed on Nov. 22, 1996, now Pat. No. 5,855,583.

(51) Int. Cl.
*A61B 17/00* (2006.01)

(52) U.S. Cl.
USPC ........................... 606/205; 74/490.03

(58) Field of Classification Search
USPC ...................... 606/1, 130, 205, 208; 600/102; 74/490.03
See application file for complete search history.

(56) References Cited

U.S. PATENT DOCUMENTS

| | | |
|---|---|---|
| 977,825 A | 12/1910 | Murphy |
| 1,327,577 A | 1/1920 | Turner |
| 3,171,549 A | 3/1965 | Orloff |
| 3,280,991 A | 10/1966 | Melton et al. |
| 3,628,535 A | 12/1971 | Ostrowsky et al. |
| 4,058,001 A | 11/1977 | Waxman |
| 4,128,880 A | 12/1978 | Cray, Jr. |
| 4,221,997 A | 9/1980 | Flemming |
| 4,367,998 A | 1/1983 | Causer |
| 4,401,852 A | 8/1983 | Noso et al. |

(Continued)

FOREIGN PATENT DOCUMENTS

| | | |
|---|---|---|
| DE | 9204118 | 7/1992 |
| DE | 9409979 U1 | 9/1994 |

(Continued)

OTHER PUBLICATIONS

EP Patent Application No. 08017470.9 Extended European Search Report, mailed Oct. 28, 2009, 6 pages.

(Continued)

*Primary Examiner* — Victor Nguyen

(57) ABSTRACT

The present invention is a device having a rigidly linked jaw that is decoupled from an articulating wrist. The device provides for articulating motion as well as actuation that may be used in grasping, cutting, suturing or the like.

7 Claims, 3 Drawing Sheets

(56) References Cited

U.S. PATENT DOCUMENTS

| | | | |
|---|---|---|---|
| 4,456,961 | A | 6/1984 | Price et al. |
| 4,460,302 | A | 7/1984 | Moreau et al. |
| 4,474,174 | A | 10/1984 | Petruzzi |
| 4,491,135 | A | 1/1985 | Klein |
| 4,503,854 | A | 3/1985 | Jako |
| 4,517,963 | A | 5/1985 | Michel |
| 4,523,884 | A | 6/1985 | Clement et al. |
| 4,586,398 | A | 5/1986 | Yindra |
| 4,604,016 | A | 8/1986 | Joyce |
| 4,616,637 | A | 10/1986 | Caspari et al. |
| 4,624,011 | A | 11/1986 | Watanabe et al. |
| 4,633,389 | A | 12/1986 | Tanaka et al. |
| 4,635,292 | A | 1/1987 | Mori et al. |
| 4,641,292 | A | 2/1987 | Tunnell et al. |
| 4,655,257 | A | 4/1987 | Iwashita |
| 4,672,963 | A | 6/1987 | Barken |
| 4,676,243 | A | 6/1987 | Clayman |
| 4,728,974 | A | 3/1988 | Nio et al. |
| 4,762,455 | A | 8/1988 | Coughlan et al. |
| 4,791,934 | A | 12/1988 | Brunnett |
| 4,791,940 | A | 12/1988 | Hirschfeld et al. |
| 4,794,912 | A | 1/1989 | Lia |
| 4,815,006 | A | 3/1989 | Andersson et al. |
| 4,815,450 | A | 3/1989 | Patel |
| 4,837,734 | A | 6/1989 | Ichikawa et al. |
| 4,852,083 | A | 7/1989 | Niehaus et al. |
| 4,853,874 | A | 8/1989 | Iwamoto et al. |
| 4,854,301 | A | 8/1989 | Nakajima |
| 4,860,215 | A | 8/1989 | Seraji |
| 4,863,133 | A | 9/1989 | Bonnell |
| 4,883,400 | A | 11/1989 | Kuban et al. |
| 4,930,494 | A | 6/1990 | Takehana et al. |
| 4,945,479 | A | 7/1990 | Rusterholz et al. |
| 4,949,717 | A | 8/1990 | Shaw |
| 4,954,952 | A | 9/1990 | Ubhayakar et al. |
| 4,965,417 | A | 10/1990 | Massie |
| 4,969,709 | A | 11/1990 | Sogawa et al. |
| 4,969,890 | A | 11/1990 | Sugita et al. |
| 4,979,933 | A | 12/1990 | Runge |
| 4,979,949 | A | 12/1990 | Matsen, III et al. |
| 4,980,626 | A | 12/1990 | Hess et al. |
| 4,989,253 | A | 1/1991 | Liang et al. |
| 4,996,975 | A | 3/1991 | Nakamura |
| 5,019,968 | A | 5/1991 | Wang et al. |
| 5,020,001 | A | 5/1991 | Yamamoto et al. |
| 5,053,687 | A | 10/1991 | Merlet |
| 5,065,741 | A | 11/1991 | Uchiyama et al. |
| 5,078,140 | A | 1/1992 | Kwoh |
| 5,086,401 | A | 2/1992 | Glassman et al. |
| 5,091,656 | A | 2/1992 | Gahn |
| 5,097,829 | A | 3/1992 | Quisenberry |
| 5,097,839 | A | 3/1992 | Allen |
| 5,098,426 | A | 3/1992 | Sklar et al. |
| 5,105,367 | A | 4/1992 | Tsuchihashi et al. |
| 5,109,499 | A | 4/1992 | Inagami et al. |
| 5,123,095 | A | 6/1992 | Papadopoulos et al. |
| 5,131,105 | A | 7/1992 | Harrawood et al. |
| 5,142,930 | A | 9/1992 | Allen et al. |
| 5,145,227 | A | 9/1992 | Monford, Jr. |
| 5,166,513 | A | 11/1992 | Keenan et al. |
| 5,175,694 | A | 12/1992 | Amato |
| 5,182,641 | A | 1/1993 | Diner et al. |
| 5,184,601 | A | 2/1993 | Putman |
| 5,187,574 | A | 2/1993 | Kosemura et al. |
| 5,196,688 | A | 3/1993 | Hesse et al. |
| 5,201,325 | A | 4/1993 | McEwen et al. |
| 5,201,743 | A | 4/1993 | Haber et al. |
| 5,217,003 | A | 6/1993 | Wilk |
| 5,221,283 | A | 6/1993 | Chang |
| 5,228,429 | A | 7/1993 | Hatano |
| 5,230,623 | A | 7/1993 | Guthrie et al. |
| 5,236,432 | A | 8/1993 | Matsen, III et al. |
| 5,239,883 | A | 8/1993 | Rosheim |
| 5,251,127 | A | 10/1993 | Raab |
| 5,257,999 | A | 11/1993 | Slanetz, Jr. |
| 5,271,384 | A | 12/1993 | McEwen et al. |
| 5,275,608 | A | 1/1994 | Forman et al. |
| 5,279,309 | A | 1/1994 | Taylor et al. |
| 5,282,806 | A | 2/1994 | Haber et al. |
| 5,282,826 | A | 2/1994 | Quadri |
| 5,289,273 | A | 2/1994 | Lang |
| 5,289,365 | A | 2/1994 | Caldwell et al. |
| 5,299,288 | A | 3/1994 | Glassman et al. |
| 5,300,926 | A | 4/1994 | Stoeckl |
| 5,303,148 | A | 4/1994 | Mattson et al. |
| 5,304,185 | A | 4/1994 | Taylor |
| 5,305,203 | A | 4/1994 | Raab |
| 5,305,427 | A | 4/1994 | Nagata |
| 5,309,717 | A | 5/1994 | Minch |
| 5,313,306 | A | 5/1994 | Kuban et al. |
| 5,320,630 | A | 6/1994 | Ahmed |
| 5,337,732 | A | 8/1994 | Grundfest et al. |
| 5,339,799 | A | 8/1994 | Kami et al. |
| 5,343,385 | A | 8/1994 | Joskowicz et al. |
| 5,343,391 | A | 8/1994 | Mushabac |
| 5,345,538 | A | 9/1994 | Narayannan et al. |
| 5,357,962 | A | 10/1994 | Green |
| 5,368,015 | A | 11/1994 | Wilk |
| 5,368,428 | A | 11/1994 | Hussey et al. |
| 5,371,536 | A | 12/1994 | Yamaguchi |
| 5,382,885 | A | 1/1995 | Salcudean et al. |
| 5,388,987 | A | 2/1995 | Badoz et al. |
| 5,395,369 | A | 3/1995 | McBrayer et al. |
| 5,397,323 | A | 3/1995 | Taylor et al. |
| 5,402,801 | A | 4/1995 | Taylor |
| 5,403,319 | A | 4/1995 | Matsen, III et al. |
| 5,408,409 | A | 4/1995 | Glassman et al. |
| 5,410,638 | A | 4/1995 | Colgate et al. |
| 5,417,210 | A | 5/1995 | Funda et al. |
| 5,417,701 | A | 5/1995 | Holmes |
| 5,422,521 | A | 6/1995 | Neer et al. |
| 5,431,645 | A | 7/1995 | Smith et al. |
| 5,434,457 | A | 7/1995 | Josephs et al. |
| 5,442,728 | A | 8/1995 | Kaufman et al. |
| 5,445,166 | A | 8/1995 | Taylor |
| 5,451,924 | A | 9/1995 | Massimino et al. |
| 5,454,827 | A | 10/1995 | Aust et al. |
| 5,455,766 | A | 10/1995 | Scheller et al. |
| 5,458,547 | A | 10/1995 | Teraoka et al. |
| 5,458,574 | A | 10/1995 | Machold et al. |
| 5,474,571 | A | 12/1995 | Lang |
| 5,476,010 | A | 12/1995 | Fleming et al. |
| 5,478,351 | A | 12/1995 | Meade et al. |
| 5,489,292 | A | 2/1996 | Tovey et al. |
| 5,490,117 | A | 2/1996 | Oda et al. |
| 5,506,912 | A | 4/1996 | Nagasaki et al. |
| 5,512,919 | A | 4/1996 | Araki |
| 5,515,478 | A | 5/1996 | Wang |
| 5,544,654 | A | 8/1996 | Murphy et al. |
| 5,553,198 | A | 9/1996 | Wang et al. |
| 5,562,503 | A | 10/1996 | Ellman et al. |
| 5,571,110 | A | 11/1996 | Matsen, III et al. |
| 5,572,999 | A | 11/1996 | Funda et al. |
| 5,609,560 | A | 3/1997 | Ichikawa et al. |
| 5,626,595 | A | 5/1997 | Sklar et al. |
| 5,629,594 | A | 5/1997 | Jacobus et al. |
| 5,630,431 | A | 5/1997 | Taylor |
| 5,631,973 | A | 5/1997 | Green |
| 5,636,259 | A | 6/1997 | Khutoryansky et al. |
| 5,649,956 | A | 7/1997 | Jensen et al. |
| 5,657,429 | A | 8/1997 | Wang et al. |
| 5,658,250 | A | 8/1997 | Blomquist et al. |
| 5,676,673 | A | 10/1997 | Ferre et al. |
| 5,693,071 | A | 12/1997 | Gorecki et al. |
| 5,695,500 | A | 12/1997 | Taylor et al. |
| 5,696,574 | A | 12/1997 | Schwaegerle |
| 5,696,837 | A | 12/1997 | Green |
| 5,715,729 | A | 2/1998 | Toyama et al. |
| 5,718,038 | A | 2/1998 | Takiar et al. |
| 5,727,569 | A | 3/1998 | Benetti et al. |
| 5,735,290 | A | 4/1998 | Sterman et al. |
| 5,737,711 | A | 4/1998 | Abe |
| 5,740,699 | A | 4/1998 | Ballantyne et al. |
| 5,749,362 | A | 5/1998 | Funda et al. |

(56) References Cited

U.S. PATENT DOCUMENTS

| | | | |
|---|---|---|---|
| 5,754,741 | A | 5/1998 | Wang et al. |
| 5,762,458 | A | 6/1998 | Wang et al. |
| 5,766,126 | A | 6/1998 | Anderson |
| 5,776,126 | A | 7/1998 | Wilk et al. |
| 5,779,623 | A | 7/1998 | Bonnell |
| 5,792,135 | A | 8/1998 | Madhani et al. |
| 5,792,178 | A | 8/1998 | Welch et al. |
| 5,797,900 | A | 8/1998 | Madhani et al. |
| 5,800,423 | A | 9/1998 | Jensen |
| 5,807,284 | A | 9/1998 | Foxlin |
| 5,807,377 | A | 9/1998 | Madhani et al. |
| 5,807,378 | A | 9/1998 | Jensen et al. |
| 5,808,665 | A | 9/1998 | Green |
| 5,810,879 | A | 9/1998 | De Guillebon |
| 5,810,880 | A | 9/1998 | Jensen et al. |
| 5,813,813 | A | 9/1998 | Daum et al. |
| 5,814,038 | A | 9/1998 | Jensen et al. |
| 5,817,084 | A | 10/1998 | Jensen |
| 5,825,982 | A | 10/1998 | Wright et al. |
| 5,836,869 | A | 11/1998 | Kudo et al. |
| 5,844,824 | A | 12/1998 | Newman et al. |
| 5,855,583 | A | 1/1999 | Wang et al. |
| 5,859,934 | A | 1/1999 | Green |
| 5,860,995 | A * | 1/1999 | Berkelaar .................... 606/174 |
| 5,876,325 | A | 3/1999 | Mizuno et al. |
| 5,878,193 | A | 3/1999 | Wang et al. |
| 5,882,206 | A | 3/1999 | Gillio |
| 5,887,121 | A | 3/1999 | Funda et al. |
| 5,904,702 | A | 5/1999 | Ek et al. |
| 5,906,630 | A | 5/1999 | Anderhub et al. |
| 5,931,832 | A | 8/1999 | Jensen |
| 5,938,678 | A | 8/1999 | Zirps et al. |
| 5,950,629 | A | 9/1999 | Taylor et al. |
| 5,951,475 | A | 9/1999 | Gueziec et al. |
| 5,951,587 | A | 9/1999 | Qureshi et al. |
| 5,954,731 | A | 9/1999 | Yoon |
| 5,980,782 | A | 11/1999 | Hershkowitz et al. |
| 5,984,932 | A | 11/1999 | Yoon |
| 6,024,695 | A | 2/2000 | Taylor et al. |
| 6,102,850 | A | 8/2000 | Wang et al. |
| 6,120,433 | A | 9/2000 | Mizuno et al. |
| 6,132,441 | A * | 10/2000 | Grace .................... 606/147 |
| 6,196,081 | B1 | 3/2001 | Yau |
| 6,270,453 | B1 | 8/2001 | Sakai |
| 6,307,285 | B1 | 10/2001 | Delson et al. |
| 6,312,435 | B1 | 11/2001 | Wallace et al. |
| 6,330,837 | B1 | 12/2001 | Charles et al. |
| 6,436,107 | B1 | 8/2002 | Wang et al. |
| 6,699,235 | B2 | 3/2004 | Wallace et al. |
| 6,793,669 | B2 | 9/2004 | Nakamura et al. |
| RE43,049 | E | 12/2011 | Grace |
| 8,292,916 | B2 | 10/2012 | Grace |
| 2008/0103524 | A1 | 5/2008 | Grace |

FOREIGN PATENT DOCUMENTS

| | | | |
|---|---|---|---|
| DE | 4310842 | | 1/1995 |
| DE | 29803734 | U1 | 4/1998 |
| EP | 239409 | | 9/1987 |
| EP | 424687 | | 5/1991 |
| EP | 776738 | | 6/1997 |
| WO | 9104711 | | 4/1991 |
| WO | 9220295 | | 11/1992 |
| WO | 9313916 | | 7/1993 |
| WO | 9418881 | | 9/1994 |
| WO | 9426167 | | 11/1994 |
| WO | 9715240 | | 5/1997 |
| WO | 9825666 | | 6/1998 |
| WO | 9834543 | A1 | 8/1998 |
| WO | 9858589 | A1 | 12/1998 |

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

Abstract of a presentation "3-D Vision Technology Applied to Advanced Minimally Invasive Surgery Systems," (Session 15/3) given at the 3rd World Congress of Endoscopic Surgery in Bordeaux, Jun. 18-20, 1992, 1 page.

Abstract of a presentation "A Pneumatic Controlled Sewing Device for Endoscopic Application the MIS Sewing Instrument MSI" given at the 3rd World Congress of Endoscopic Surgery in Bordeaux, Jun. 18-20, 1992, 1 page.

Abstract of a presentation given at the 3rd World Congress of Endoscopic Surgery in Bordeaux entitled "Session 15/1", Jun. 18-20, 1992, 1 page.

Abstract of a presentation given at the 3rd World Congress of Endoscopic Surgery in Bordeaux, entitled "Session 15/2", Jun. 18-20, 1992, 1 page total.

Abstract of a presentation given at the 3rd World Congress of Endoscopic Surgery in Bordeaux entitled "Session 15/4", Jun. 18-20, 1992, 1 page.

Abstract of a presentation given at the 3rd World Congress of Endoscopic Surgery in Bordeaux entitled "Session 15/5", Jun. 18-20, 1992, 1 page.

Bejczy, Antal K. et al., "Controlling Remote Manipulators through Kinesthetic Coupling," Computers in Mechanical Engineering, 1983, pp. 48-60, vol. 1—Issue 1.

Ben Gayed, M. et al., "An Advanced Control Micromanipulator for Surgical Applications," Systems Science, 1987, pp. 123-134, vol. 13.

Besant, Colin et al., Abstract of presentation "Camera Control for Laparoscopic Surgery by Speech recognizing Robot: Constant Attention and Better Use of Personnel," 3rd World Congress of Endoscopic surgery, 1993, p. 271, vol. 3—issue 3.

Charles, Steve et al., "Design of a Surgeon Machine Interface for Teleoperated Microsurgery," Proceedings of IEEE Annual Conference on Engineering in Medicine and Biology, 1989, pp. 0883-0884, vol. 11, IEEE.

Colgate, Edward, J., "Power and Impedance Scaling in Bilateral Manipulation," IEEE International Conference on Robotics and Automation, Sacramento, California, Apr. 1991, pp. 2292-2297, vol. 3, IEEE.

Corcoran, Elizabeth, "Robots for the Operating Room," The New York Times, 2 pages total, Jul. 19, 1992, Section 3 p. 9C.

Das, Hari et al., "Kinematic Control and Visual Display of Redundant Teleoperators," IEEE International Conference on Systems, Man, and Cybernetics, 1989, pp. 1072-1077, vol. 3, IEEE.

Dolan, J.M. et al., "A Robot in an Operating Room: A Bull in a China Shop," 1987, pp. 1096-1097, vol. 2.

Green, Philip S. et al., Abstract of a presentation, "Telepresence: Advanced Teleoperator Technology for Minimally Invasive Surgery," 1992 Medicine Meets Virtual Reality (MMVR) symposium in San Diego, Jun. 4-7, 1992, 1 page.

Green, Philip S. et al., Statutory Declaration by Dr. Phillip S. Green, the presenter of the video entitled "Telepresence Surgery: The Future of Minimally Invasive Medicine," European Patent Convention in the Matter of EP-B-653922. 32 pages, Sep. 12, 2000.

Guerrouad, Aicha et al., "SMOS: Stereotaxical Microtelemanipulator for Ocular Surgery," IEEE Engineering in Medicine & Biology Society 11th annual international conference, Nov. 9-12, 1989, pp. 879-880, vol. 3, IEEE.

Inoue, Masao; "Six-Axis bilateral control of an articulated slave manipulator using a Cartesian master manipulator," Advanced robotics, 1990, pp. 139-150, vol. 4—Issue 2, Robotic society of Japan.

Jau, B. M., "Anthropomorphic Remote Manipulator," NASA Tech Briefs, Apr. 1991, p. 92, NASA's Jet Propulsion Laboratory, Pasadena, California.

Kazerooni, H., "Human/Robot Interaction via the Transfer of Power and Information Signals Part I: Dynamics and Control Analysis," IEEE International Conference on Robotics and Automation, 1989, pp. 1632-1640, IEEE.

Kazerooni, H, "Human/Robot Interaction via the Transfer of Power and Information Signals—Part II," An Experimental Analysis, Proc. of the 1989 IEEE International Conference on Robotics and Automation, 1989, pp. 1641-1647, vol. 3, IEEE.

(56) References Cited

OTHER PUBLICATIONS

Krishnan, S.M. et al., Abstract of a presentation "Design Considerations of a New Generation Endoscope Using Robotics and Computer Vision Technology," given at the 3rd World Congress of Endoscopic Surgery in Bordeaux, Jun. 18-20, 1992, 1 page.

Lavallee, Stephane, "A New System for Computer Assisted Neurosurgery," IEEE Eng. in Med. & Biol. Soc. 11th Annual International Conference, Jun. 1989, pp. 926-927, vol. 11.

Mair, Gordon M., Industrial Robotics, Prentice Hall, 1988, pp. 41-43, 49-50, 54, 203-209.

Majima S. et al., "On a Micro Manipulator for Medical Application Stability Consideration of its Bilateral Controller Mechatronics," 1991, pp. 293-309, vol. 1—Issue 3.

Melzer, Abstract of a presentation "Concept and Experimental Application of a Surgical Robotic System the Steerable MIS Instrument SMI," given at the 3rd World Congress of Endoscopic Surgery in Bordeaux, Jun. 18-20, 1992, 1 page total.

Preising, B. et al., "A Literature Review: Robots in Medicine," IEEE Engineering in Medicine and Biology, 1991, pp. 13-22, 71, vol. 10—Issue 2, IEEE.

Sabatini, A. M. et al., "Force Feedback Based Telemicromanipulation for Robot Surgery on Soft Tissue," IEEE Engineering in Medicine and Biology Society 11th Annual International Conference, 1989, pp. 890-891, vol. 3, IEEE.

Taubes, Gary et al., "Surgery in Cyberspace," Discover magazine, Dec. 1994, vol. 15, issue 12, pp. 85-92.

Taylor, Russell H. et al., "Taming the Bull: Safety in a Precise Surgical Robot," Fifth International Conference on Advanced Robotics (91 ICAR), Jun. 19-22, 1991, vol. 1, pp. 865-870, IEEE.

Tejima, Noriyuki et al., "A New Microsurgical Robot System for Corneal Transplantation," Precision Machinery, 1988, pp. 1-9, vol. 2, Gordon and Breach Science Publishers Inc.

Tendick Frank, et al., "Analysis of the Surgeon's Grasp for Telerobotic Surgical Manipulation," IEEE 11th Annual Int Conf on Engineering in Medicine and Biology, Jun. 1989, pp. 914-915, IEEE.

Thring, M.W., Robots and Telechirs: Manipulators with Memory; Remote Manipulators; Machine Limbs for the Handicapped, 1983, pp. 9-11, 108-131, 194-195, 235-279; Ellis Horwood Limited, Chapter 5,7,8,9.

Transcript of a video presented by SRI at the 3rd World Congress of Endoscopic Surgery in Bordeaux, France on Jun. 18-20, 1992; in Washington D.C. on Apr. 9, 1992; and in San Diego, CA on Jun. 4-7, 1992; entitled "Telepresence Surgery: The Future of Minimally Invasive Medicine," 3 pages.

Trevelyan, James P. et al., "Motion Control for a Sheep Shearing Robot," IEEE Robotics Research Conference, the 1st International Symposium, Carroll, NH, USA., 1983, pp. 175-190, in Robotics Research, MIT Press.

Vibet, C., "Properties of Master Slave Robots," Motor-con, 1987, pp. 309-316.

Wolf, Stanley et al., Student Reference Manual for Electronic Instrumentation Laboratories, 1990, pp. 498 and 499, Prentice Hall New Jersey.

PCT/US00/09201 International Search Report, mailed Aug. 30, 2000, 1 page.

Supplementary European Search Report for Application No. EP00914788, mailed on Mar. 11, 2009, 5 pages.

\* cited by examiner

RIGIDLY-LINKED ARTICULATING WRIST WITH DECOUPLED MOTION TRANSMISSION

CROSS-REFERENCE TO RELATED APPLICATIONS

This application is a continuation-in-part of application Ser. No. 09/262,134, filed Mar. 3, 1999, which is a continuation-in-part of application Ser. No. 08/873,190, filed Jun. 11, 1997, now U.S. Pat. No. 6,102,850, which is a continuation-in-part of application Ser. No. 08/755,063, filed Nov. 22, 1996, now U.S. Pat. No. 5,855,583.

BACKGROUND OF THE INVENTION

1. Field of the Invention

The present invention generally relates to surgical devices. More particularly, the present invention relates to a device for suturing during the performance of minimally invasive endoscopic surgical procedures and more particularly to an articulating device for use in endoscopic coronary artery by-pass grafting surgery.

2. Description of Related Art

Blockage of a coronary artery may deprive the heart of the blood and oxygen required to sustain life. The blockage may be removed with medication or by an angioplasty. For severe blockage, a coronary artery bypass graft (CABG) is performed to bypass the blocked area of the artery. CABG procedures are typically performed by splitting the sternum and pulling open the chest cavity to provide access to the heart. An incision may be made in the artery adjacent to the blocked area. The internal mammary artery (IMA) or some other arterial source of blood-flow may then be severed and attached to the artery at the point of incision. The IMA bypasses the blocked area of the artery to again provide a full flow of blood to the heart.

Splitting the sternum and opening the chest cavity can create tremendous trauma on the patient. Additionally, the cracked sternum prolongs the recovery period of the patient. As such, there have been developed systems that enable minimally invasive CABG procedures. These systems utilize hand held tools and small incisions, on the order of 3-5 inches in length, to provide access to the thoracic region of a patient.

Such minimally invasive procedures are conducted by inserting surgical instruments through small incisions, on the order of inches in the skin of the patient. Manipulating such instruments can be awkward, particularly when suturing a graft to an artery. These systems utilize direct visualization of the surgical site. Such systems do not enable a completely endoscopic approach to the CABG procedure because of the need for direct visualization of the site. Additionally, such systems do not enable a fully endoscopic approach because of the incision size necessary to adequately manipulate the surgical instruments at the surgical site.

A fully endoscopic approach utilizes small holes to provide access to the thoracic cavity. Each of these holes is on the order of 3-11 mm in diameter. In order to perform a CABG procedure in a fully endoscopic fashion (i.e. using 3-11 mm holes) a robotic system must be used to filter hand tremors and scale motions made by the surgeon.

To facilitate the performance of an endoscopic surgical procedure, it would be useful to employ surgical instruments that can maneuver to the surgical site as well as manipulate tissue or sutures to perform an anastomosis.

To help minimize risk to the patient, and to minimize operating time, what is needed in the art is a robotically actuated surgical device that can articulate as well as actuate without being overly complex in design.

SUMMARY OF THE INVENTION

The present invention is an articulating device for tissue and needle manipulation, the device comprising:

An elongated housing having a proximal end and a distal end;

an articulation rod extending interior the housing, the articulation rod having a proximal end and a distal end;

an actuation rod extending interior the housing, the actuation rod having a proximal end and a distal end;

a rack driver in communication with the actuation rod at the distal end thereof, the rack driver engaged with a cylindrical rack for translating the motion of the actuation rod substantially about ninety degrees; and a jaw in communication with the cylindrical rack, whereby movement of the cylindrical rack actuates the jaw, the jaw further in pivotal communication with the articulation rod such that linear movement of the articulation rod produces rotational movement of the jaw.

DETAILED DESCRIPTION OF THE INVENTION

Figure 1:
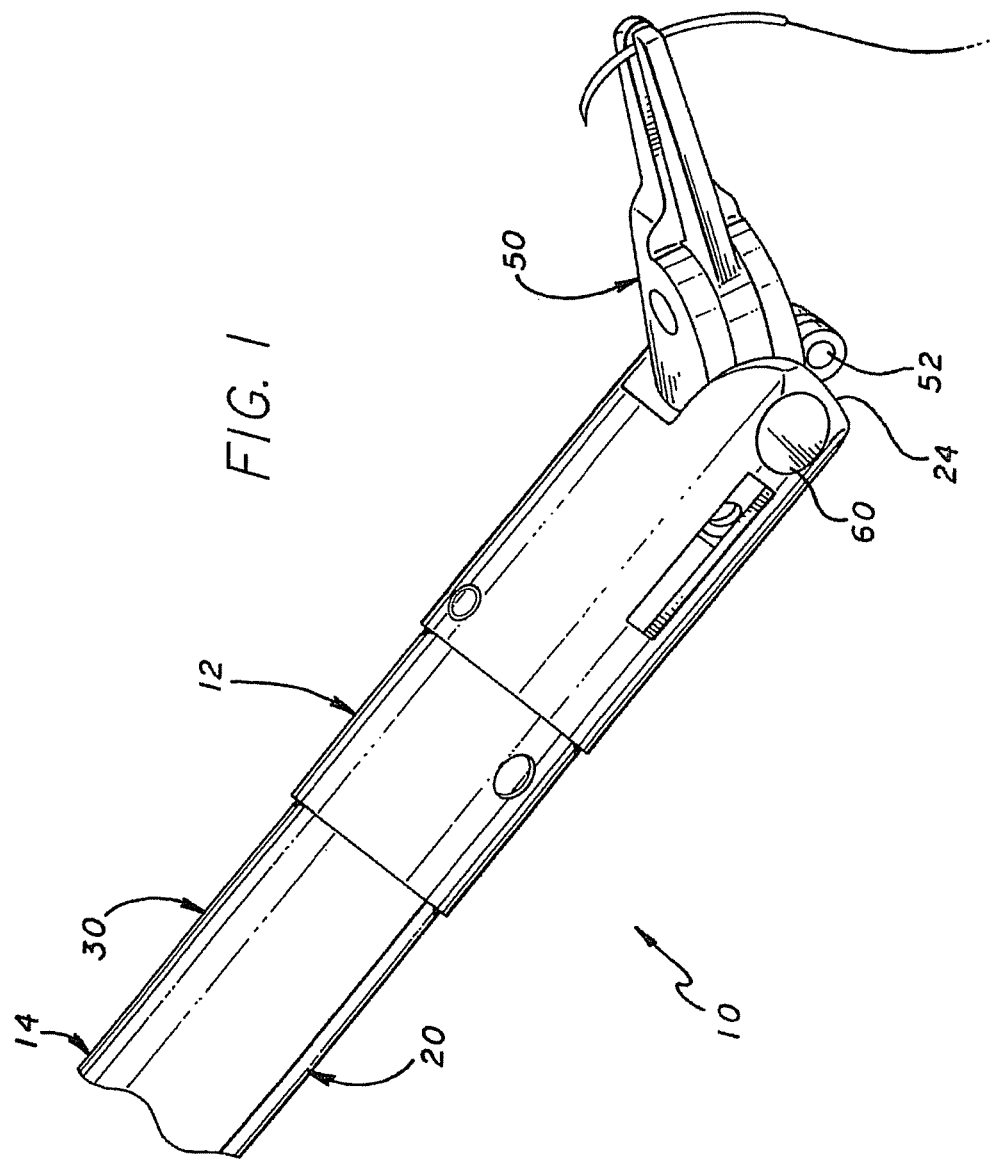
FIG. 1 is a partial break-away perspective view of a device in accordance with the present invention in a closed angled configuration.
Figure 2:
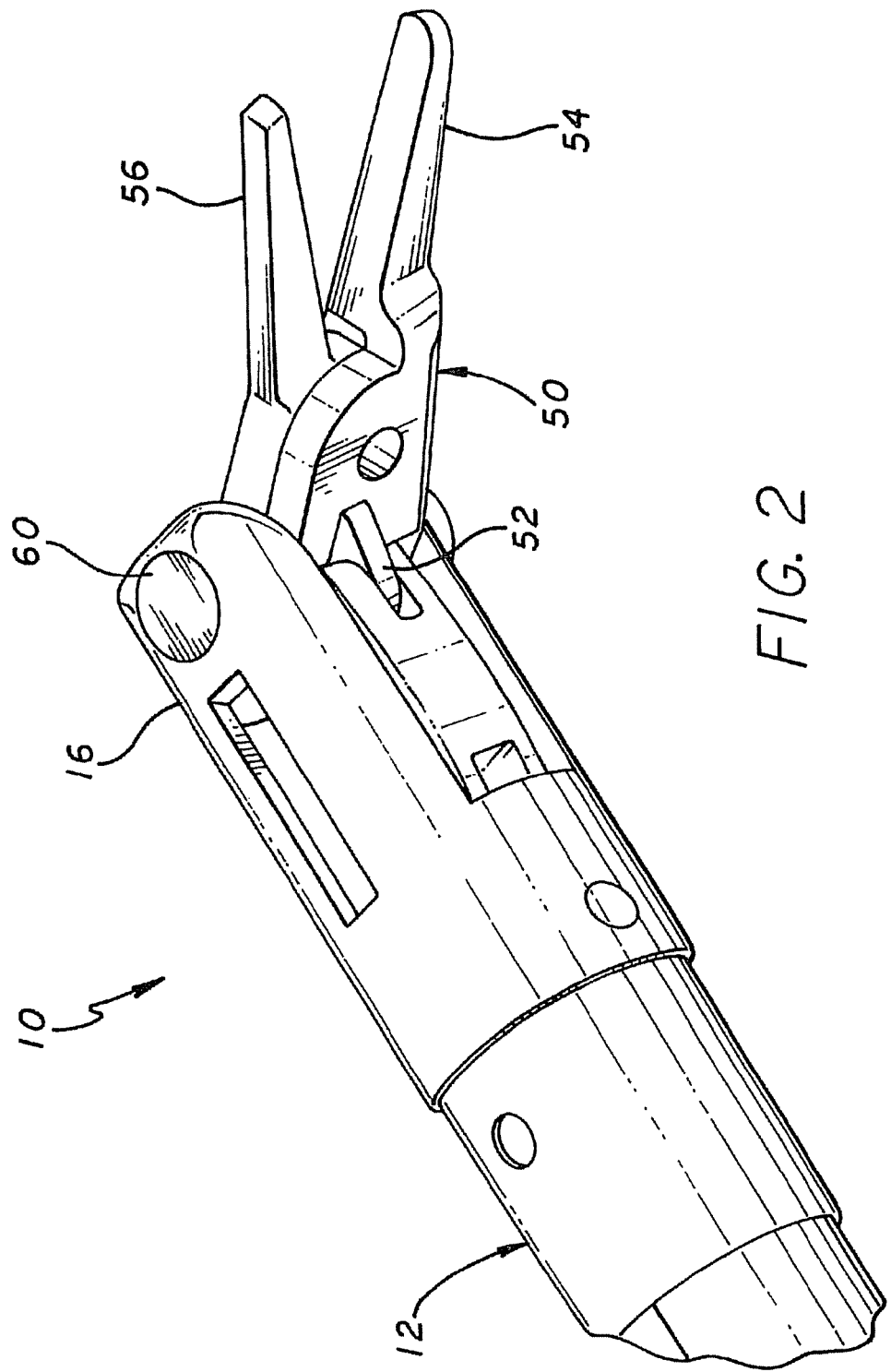
FIG. 2 is a partial break-away perspective view of a device in accordance with the present invention in an open angled configuration.
Figure 3:
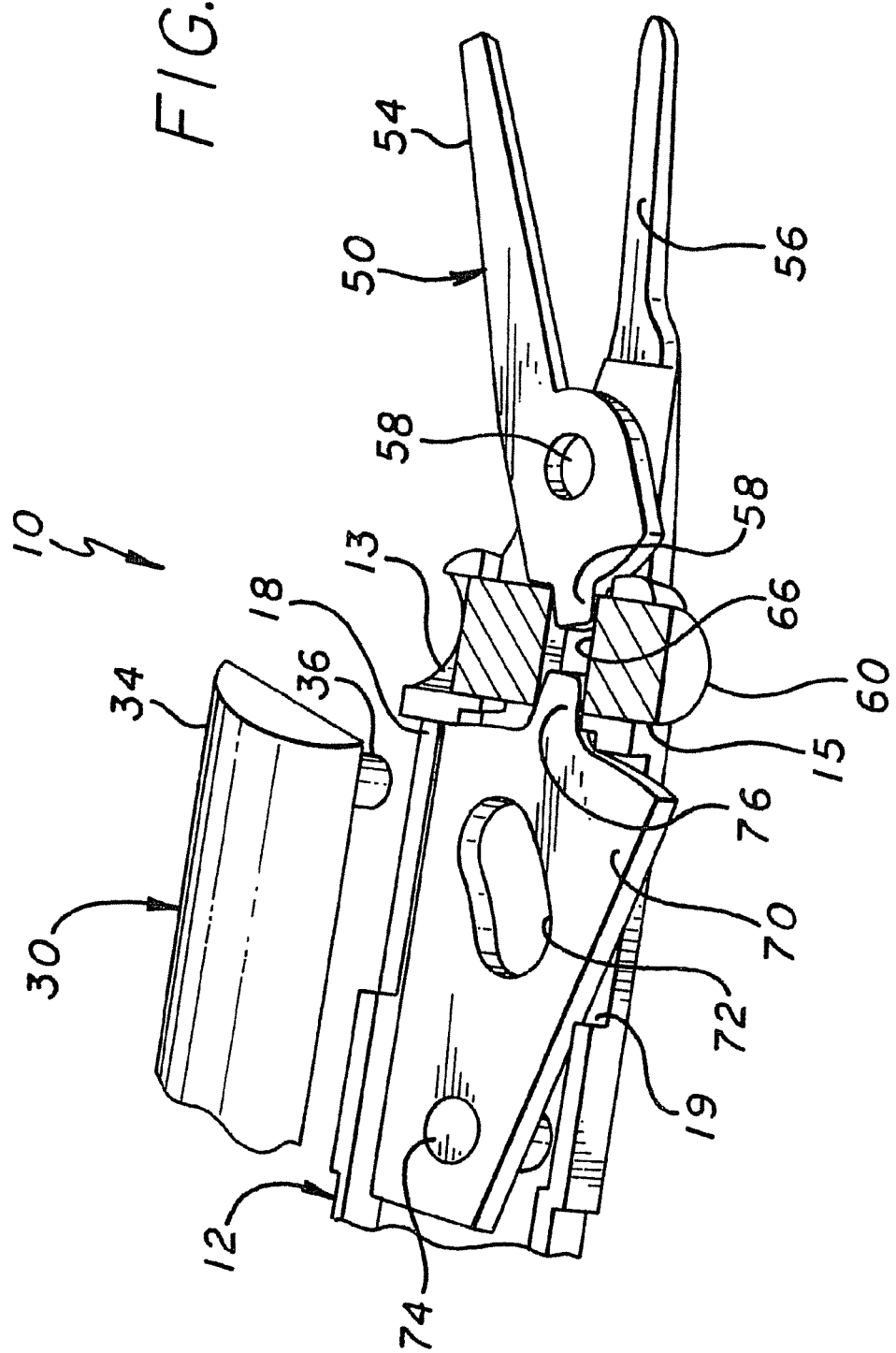
FIG. 3 is a cross-sectional perspective view of a device in accordance with the present invention in an opened straight configuration.

Referring to the drawings more particularly by reference numbers, FIGS. 1, 2 and 3 show a preferred embodiment of the articulating actuating device 10. The device 10 includes a housing 12. The housing extends substantially the length of the instrument 10 and has a proximal end 14 and a distal end 16 and a longitudinal axis X. Disposed interiorly the housing 12 is an articulation rod 20 and an actuation rod 30. Each of the articulation rod 20 and the actuation rod 30 have respective proximal ends 22, 32 and distal ends 24, 34.

The proximal ends 22, 32 of the rods may be attached to a robotic system for the performance of minimally invasive surgical procedures. One such system is produced by Computer Motion, Inc. The assignee hereof and is described in U.S. Pat. No. 5,855,583, which is incorporated herein by reference.

The rods 20, 30 are attached to actuators via attachment means taught in U.S. Pat. No. 5,855,583. Other means for removably attaching a rod to an actuator are known in the art including the use of screws, clips or the like. In this way, each of the rods 20, 30 may be driven by the actuator which is connected to various user interfaces and power sources and are conducive to the performance of minimally invasive surgical procedures.

The articulation rod 20 extends substantially the length of the housing 12 along its longitudinal axis X. The articulation rod 20 is pivotally connected to a jaw 50. Such a pivotal connection may be accomplished through the use of a hinge 52 attached intermediate the articulation rod 20 and the jaw 50.

The jaw 50 pivotally communicates with the housing 12 at the distal end 16 thereof through the use of a rack 60. In this way, motion of the articulation rod 20 results in rotation of the jaw 50. The rack 60 provides a pivot about which the jaw 50 rotates.

The actuation rod 30 provides for actuation of the jaw 50. The actuation rod has a pin 36 disposed at the distal end 34 thereof. The pin 36 seats in a rack channel 72 disposed in a rack driver 70. The rack driver is pivotally attached to the housing 12 via a pin 74 or the like. The housing has two longitudinal apertures 18, 19 formed therethrough at the distal end 16 thereof to provide for lateral movement of the rack driver 70 which shall be described in detail hereinbelow.

Longitudinal motion of the actuation rod 30 moves the pin 36 in the rack channel 72 which translates the longitudinal motion of the actuation rod 30 into a pivotal motion of the rack driver 70. The rack driver 70 pivots about the pivot point defined by the pin 74 which attaches the rack driver 70 to the housing 12. The rack driver 70 may move outside of the space defined as the interior of the housing through the longitudinal apertures 18, 19.

The rack driver 70 has a shoulder 76 which engages the rack 60. As the rack driver 70 pivots, the shoulder 76 causes the rack 60 to move laterally, which is orthogonal to the longitudinal motion of the actuation rod 30 and orthogonal to the longitudinal axis of the housing 12. The rack 60 is slidably moveable within the housing 12 through two cylindrical apertures 13, 15 formed therethrough. As the rack 60 moves laterally, the jaw 50 is actuated. The lateral movement of the rack 60 is transferred to a first jaw element 54. A second jaw element 56 is pivotally connected to the first jaw element 54 via a pin 58 or the like and is held stationary with respect to the first jaw element 54. In this way, as the first jaw element is 54 is moved, the second jaw element 56 remains stationary and the jaw 50 is actuated. If each element has a sharp edge, then the jaw may function as a scissors.

The jaw 50 is always in communication with the rack 60, even as it is articulated through the motion of the articulation rod 20. This is accomplished through the use of a cylindrical rack having a circumferential channel 66 formed therein. The channel 66 receives the shoulder 76 of the rack driver 70 as well as a shoulder 58 on the first jaw element 54. As such, as the jaw 50 is articulated, the shoulder 58 on the first jaw element 54 rotates within the circumferential channel 66 in the rack 60 maintaining communication therein and providing for actuation of the jaw 50 regardless of the articulated position of the jaw 50 caused through motion of the articulation rod 20.

In this fashion, the articulation of the jaw 50 and the actuation of the jaw 50 are decoupled. It is highly advantageous to provide for a rigidly linked device that is decoupled in this fashion for several reasons. First, the device is easily sterilizable and secondly, the device is quite safe to use as there is no use of tensioned cables or the like.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art.

What is claimed is:

1. A surgical instrument comprising:
   a housing having a longitudinal axis, a proximal end, and a distal end;
   a jaw element;
   coupled to rotate the jaw element about a rotation axis;
   an actuation rod having a distal end coupled to actuate the jaw element about an actuation axis, the actuation axis being orthogonal to the rotation axis;
   a hinge attached intermediate the articulation rod and the jaw element; and
   a rack coupled to the jaw element, the rack further being coupled to the articulation rod, the rack configured to rotate in response to the articulation rod being driven, the rack being a cylindrical rack having a circumferential channel formed therein.

2. The instrument of claim 1, the actuation rod comprising a pin disposed at a distal end of the actuation rod, the instrument further comprising:
   a rack driver pivotally attached to the housing, the rack driver comprising a rack channel fittingly receiving the pin of the actuation rod, the rack driver further having a distal end coupled to actuate the jaw element; wherein the rack driver comprises a shoulder engaging the rack.

3. The instrument of claim 1, wherein at least one of the actuation rod and the articulation rod is removably attached to a corresponding actuator.

4. The instrument of claim 1, further comprising a second jaw element, wherein the second jaw element is held stationary with respect to the jaw element.

5. The instrument of claim 1, the articulation rod and the actuation rod being provided interior to the housing.

6. A surgical instrument comprising:
   a housing having a longitudinal axis, a proximal end, and a distal end;
   a jaw element;
   coupled to rotate the jaw element about a rotation axis;
   an actuation rod having a distal end coupled to actuate the jaw element about an actuation axis, the actuation axis being orthogonal to the rotation axis;
   the actuation rod comprising a pin disposed at a distal end of the actuation rod, the instrument further comprising:
   a rack driver pivotally attached to the housing, the rack driver comprising a rack channel fittingly receiving the pin of the actuation rod, the rack driver further having a distal end coupled to actuate the jaw element.

7. A surgical instrument comprising:
   a housing having a longitudinal axis, a proximal end, and a distal end;
   a jaw element;
   an articulation rod having a distal end coupled to rotate the jaw element about a rotation axis;
   an actuation rod having a distal end coupled to actuate the jaw element about an actuation axis, the actuation axis being orthogonal to the rotation axis;
   a hinge attached intermediate the articulation rod and the jaw element; and
   a rack coupled to the jaw element, the rack further being coupled to the articulation rod, the rack configured to rotate in response to the articulation rod being driven;
   the housing comprising longitudinal apertures at the distal end thereof.

* * * * *